United States Patent [19]

Fletcher et al.

[11] 3,996,471
[45] Dec. 7, 1976

[54] METHOD AND SYSTEM FOR IN VIVO MEASUREMENT OF BONE TISSUE USING A TWO LEVEL ENERGY SOURCE

[76] Inventors: James C. Fletcher, Administrator of the National Aeronautics and Space Admministration, with respect to an invention of John R. Cameron, Madison, Wis.; Philip F. Judy, Boston, Mass.

[22] Filed: Mar. 11, 1975

[21] Appl. No.: 557,430

[52] U.S. Cl. .............................. 250/444; 250/498; 250/363 R
[51] Int. Cl.² .......................................... G01N 21/34
[58] Field of Search .......... 250/363, 369, 361, 362, 250/439, 454, 456, 494, 496, 497, 498, 444, 491, 510, 503

[56] References Cited
UNITED STATES PATENTS

| | | |
|---|---|---|
| 3,715,587 | 2/1973 | Burkhalter et al. ............... 250/510 |
| 3,715,588 | 2/1973 | Rose .................. 250/510 |
| 3,818,220 | 6/1974 | Richards ..................... 250/445 T |
| 3,842,285 | 10/1974 | Edeline et al. .................... 250/497 |
| 3,867,634 | 2/1975 | Hounsfield ........................ 250/503 |
| 3,904,530 | 9/1975 | Martone et al. ................... 250/369 |

Primary Examiner—Alfred E. Smith
Assistant Examiner—David K. Moore
Attorney, Agent, or Firm—Edward K. Fein; John R. Manning; Marvin F. Matthews

[57] ABSTRACT

Methods and apparatus are provided for radiologically determining the bone mineral content of living human bone tissue independently of the concurrent presence of adipose and other soft tissues. A target section of the body of the subject is irradiated with a beam of penetrative radiations of preselected energy to determine the attenuation of such beam with respect to the intensity of each of two radiations of different predetermined energy levels. The resulting measurements are then employed to determine bone mineral content according to the following relationship:

$$I = (I_o) \exp [(\mu BM^\mu BM) - (\mu ST^\mu ST)]$$

wherein $I_o$ is the unattentuated intensity of the radiations in the beam, $\mu$ is the mass attenuation coefficient, M is mass in $g/cm^2$.

19 Claims, 5 Drawing Figures

U.S. Patent  Dec. 7, 1976  3,996,471
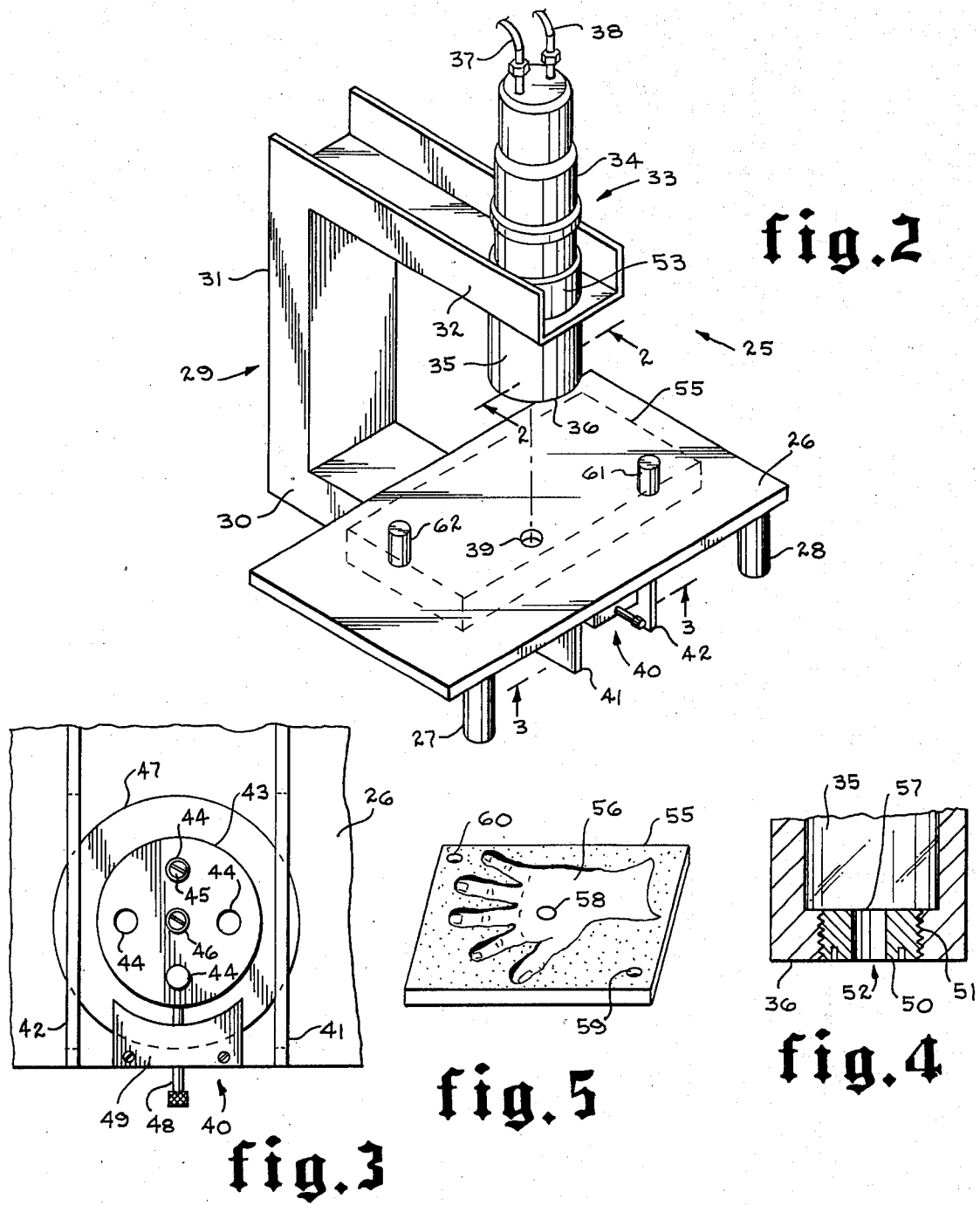
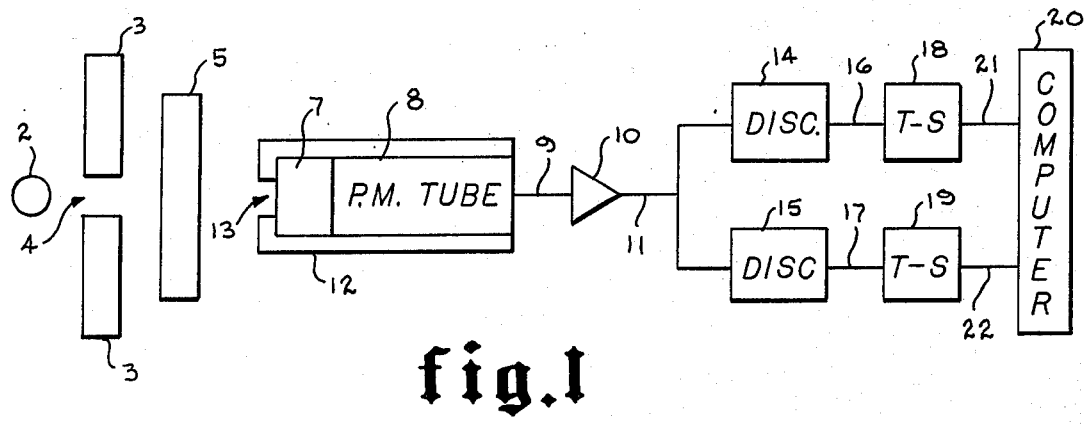

METHOD AND SYSTEM FOR IN VIVO MEASUREMENT OF BONE TISSUE USING A TWO LEVEL ENERGY SOURCE

ORIGIN OF THE INVENTION

The invention described herein was made in the performance of work under a NASA contract and is subject to the provisions of Section 305 of the National Aeronautics and Space Act of 1958, Public Law 85–568 (72 Stat. 435; 45 U.S.C. 2457)

BACKGROUND OF THE INVENTION

This invention relates to methods and apparatus for making radiological measurements of human physiological properties and more particularly relates to improved radiological methods and apparatus for measuring changes in bone tissue in a living human being.

It is well known that the bone mineral content is an important physiological characteristic with respect to the health and well-being of a person, and therefore measurements of bone mineral content are often relied upon for diagnostic purposes. The usefulness of this diagnostic technique is, however, limited by the fact that present in vivos measurements do not accurately indicate relatively small changes, and by the fact that a more accurate measurement can only be obtained by invading the body for the purpose of removing an actual sample of the person's bone tissue.

There is described in the October 11, 1963, issue of Science, pp. 230–232, a technique for traversing the subject person with a beam of monoenergetic radiation for the purpose of determining bone mineral content. Although this technique has many useful applications, and although it has the advantage of not requiring an actual invasion of the human body to obtain a sample, it nevertheless suffers from limitations with respect to accuracy. The reason for this limitation is that any section of the human body containing bone tissue will also contain substantial quantities of other soft tissues. These tissues will, of course, have a different attenuation coefficient with respect to the bombarding radiation in the beam, and thus the resulting density measurement is actually a determination of the combined density of both bone and soft tissue. Moreover, this limitation is further complicated by the fact that the soft tissues in the target section are not all of the same density, since adipose tissue tends to have only about 80% (for a specific set of X-ray energies) of the attenuating capability of that exercised by other soft tissue. Consequently, measurements based on a determination of attenuation as practiced by the foregoing technique may provide error as great as 8% of the bone mineral content sought to be measured.

Although the term "density" is commonly used in connection with radiology, it is nevertheless somewhat imprecise. If the portion of the tissue irradiated by this technique is removed and ashed, the mass of such ash will correlate closely with the measurement provided with this technique. Similarly, it will also correlate with the mass of the bone. As used herein, therefore, the term bone mineral "density" shall mean the same as the terms bone mineral "mass" or bone mineral "content," inasmuch as no other term has achieved acceptance by those having experience in this art.

These disadvantages of the prior art are overcome with the present invention, and novel measurement techniques and apparatus are hereinafter described which employ polyenergetic radiation for the purpose of establishing two different but correlative measurements of the attenuating effect had by the target material, and wherein bone mineral content may be obtained from computations employing both such measurements together with preselected factors relating to source energy and the like.

THEORY OF INVENTION

In an ideal embodiment of the present invention, the target portion of the subject's body is irradiated with photons of a predetermined higher energy to determine the attenuation characteristics of the target with respect to bone tissue, and with photons of a predetermined lower energy to determine such characteristics with respect to soft tissues in the target. The transmission of such photons through the target may be described by the following equations:

$$I_1 = (I_{o,1})\, exp\, [(-\mu_{BM,1} M_{BM}) - (\mu_{ST,1} M_{ST})] \qquad 1.$$

$$I_2 = (I_{o,2})\, exp\, [(-\mu_{BM,2} M_{BM}) - (\mu_{ST,2} M_{ST})] \qquad 2.$$

where $I_{o,1}$ equals the unattenuated intensity of the photons in the low energy beam, $I_{o,2}$ equals the unattenuated intensity of the photons in the high energy beam, $I_1$ is the attenuated intensity of the low energy beam, $I_2$ is the attenuated intensity of the high energy beam, $\mu_{BM,1}$ is the mass attenuation coefficient of the bone tissue with respect to the low energy photons, $\mu_{BM,2}$ is the mass attenuation coefficient of the bone tissue with respect to the high energy photons, $M_{BM}$ is the mass in g/cm$^2$ of bone mineral in the irradiated target, and $M_{ST}$ is the mass in g/cm$^2$ of soft tissue in the irradiated target.

As hereinbefore explained, the object of this invention is to determine the value of $M_{BM}$ and $M_{ST}$, respectively. Accordingly, equations (1) and (2) may be solved in a conventional manner to provide the following new equations:

$$M_{BM} = \left[ K_1 \log_e \left( \frac{I_{o,1}}{I_1} \right) \right] + \left[ K_2 \log_e \left( \frac{I_{o,2}}{I_2} \right) \right] \qquad (3)$$

$$M_{ST} = \left[ K_3 \log_e \left( \frac{I_{o,1}}{I_1} \right) \right] + \left[ K_4 \log_e \left( \frac{I_{o,2}}{I_2} \right) \right] \qquad (4)$$

wherein $K_1$, $K_2$, $K_3$, and $K_4$ are derived according to the following equations:

$$K_1 = \frac{\mu_{ST,2}}{D} \qquad (5)$$

-continued $$K_2 = \frac{-\mu_{ST,1}}{D} \quad (6)$$

$$K_3 = \frac{-\mu_{BM,2}}{D} \quad (7)$$

$$K_4 = \frac{\mu_{BM,1}}{D} \quad (8)$$

and wherein D is expressed as follows:

$$D = [(\mu_{BM,1})(\mu_{ST,2})] - [(\mu_{BM,2})(\mu_{ST,1})] \quad 9.$$

PRACTICE OF INVENTION

In an ideal form of the invention, apparatus is provided which includes means for establishing and directing a collimated beam of radiation onto the crystal of a scintillation counter having its photomultiplier connected to a pulse height discriminator connected to a conventional pulse timer scale. The high energy photon beam may be conveniently produced with an encapsulated quantity of an isotope such as americium −241, and the low energy beam may be produced with a quantity of iodine −125.

The crystal of the scintillation counter is preferably shielded to block all radiation except that composing the beam intended to be received, and a suitable spacing is preferably provided between the crystal and the radiation source to accommodate the target sought to be investigated. The values for $I_{o,1}$ and $I_{o,2}$ may be obtained by irradiating the crystal with unattenuated radiation from each source, or by any of several other well known techniques. The values for $I_1$ and $I_2$, however, are obtained by bombarding the crystal in a similar manner with the radiation beam penetrating and passing through the target, or a preselected time interval established by the timer scaler. The output of the timer scaler is a digital representation of the values of $I_1$ and $I_2$, respectively, and thus the output signal from the timer scaler may be fed directly into a conventional digital computer or other suitable means which has been pre-programmed according to the relationships expressed by equations (3) and (4).

The foregoing technique assumes that each photon which strikes the crystal has traversed the space between the source and the detector without engaging in an interaction with any nucleus therebetween, and that all detected radiations originated from the source. Although this assumption is not entirely correct, the crystal as well as the source may be shielded to provide that detection of radiations, other than unattenuated photons from the source, are reduced to an insignificant number. Furthermore, instead of a simple discriminator which registers all pulses of greater than a preselected amplitude, the output signal from the photomultiplier tube may be applied to a multichannel pulse height analyzer, whereby only those pulses corresponding to radiations of the type sought to be counted may be passed to the timer scaler. In this manner, spurious indications from noise or stray radiations may be reduced to statistical insignificance.

As hereinbefore stated, the target may be irradiated at different times by the high and low energy photon beam. Inasmuch as geometry is an important consideration in the making of any radiation measurement, apparatus is provided as will hereinafter be explained whereby the target and detector are held in the same configuration during both irradiation steps, and whereby only the source is changed to alter the energy level of the bombarding radiations.

Alternately, $I_1$ and $I_2$ may be obtained at the same time by simultaneously irradiating the target with a composite beam of both high and low energy radiation, inasmuch as the scintillation counter produces pulses which may be correlated with the terminal energies of the detected radiations. Thus, the irradiation steps in the technique may be employed with a source which is an encapsulated mixture having appropriate parts of both iodine −125 and americium −241. alternatively, the material in the source capsule may be an isotope such as gadolinium −153, which produces radiation of more than one predetermined energy.

These and other embodiments of the present invention will become apparent from the following detailed description, wherein reference is made to the figures in the accompanying drawings.

BRIEF DESCRIPTION OF THE DRAWINGS

FIG. 1 is a simplified functional representation of an illustrative system embodying and employing the concept of the present invention.

FIG. 2 is a pictorial representation of a particularly suitable form of apparatus exemplifying the functional concepts illustrated in FIG. 1.

FIG. 3 is a pictorial representation of a selected portion of the apparatus depicted in FIG. 2.

FIG. 4 is a pictorial representation of another selected portion of the apparatus depicted in FIG. 2.

FIG. 5 is a pictorial representation of apparatus suitable for use in conjunction with the apparatus depicted in FIGS. 2–4.

DETAILED DESCRIPTION

Referring now to FIG. 1, there may be seen a simplified functional diagram of a system for employing the concept of the present invention, and including a radiation source 2 for irradiating the specimen 5 sought to be investigated. The radiation source 2 may be an encapsulated quantity of a suitable isotope such as americium-241 or iodine-125 to produce radiations such as X-rays, gamma rays, and the like, or it may be a static atmosphere ion accelerator or other electromechanical source of gamma rays, neutrons, protons, etc. In either case, the source 2 is preferably disposed within or behind suitable shielding 3 having an aperture 4, whereby radiations are directed onto the specimen 5 in the manner of a beam.

As hereinbefore stated, it is desired to produce a measurement of the attenuation characteristics of the specimen 5. Accordingly, the specimen 5 is preferably disposed between the radiation source 2 and a suitable detector which, in this instance, is preferably a scintillation counter formed by a suitable phosphor 7 which is optically connected to a photomultiplier tube 8 having an "end window" configuration. The phosphor 7 may be any suitable type of crystal. For these purposes, however, the phosphor 7 is preferably formed of sodium iodide and thallium activated.

The phosphor 7 will scintillate in response to incident radiations from any source, of course, and not merely radiations emanating from the radiation source 2 and formed into a beam by the aperture 4 in the shield 3. Accordingly, the phosphor 7 and photomultiplier tube 8 are preferably enclosed in a cannister-type shield 12 having an aperture 13 located to expose the phosphor 7 to substantially only the radiations in the beam produced by the aperture 4 in the shield 3.

As is well known to those experienced in this technology, each radiation absorbed by the phosphor 7 will create a discrete flash of light in the phosphor 7 which, in turn, has an intensity functionally related to the terminal energy of the captured radiation. This light flash or scintillation is "seen" by a photo-responsive cathode in the tube 8 which, in turn, generates a voltage pulse having an amplitude functionally related to the intensity of the light flash produced in the phosphor 7. Accordingly, the output signal 9 from the photomultiplier tube 8 is composed of a train of voltage pulses which are functionally representative of the number and energy of the radiation emanating from the radiation source 2 and bombarding the phosphor 7.

Basically, the attenuation characteristic of the specimen 5 to be investigated is a function of its capability to capture or scatter radiations emanating from the radiation source. In other words, the basic measurement is a function of the difference between the number of radiations which strike the phosphor 7 when the specimen 5 is not located in the beam, and the number of radiations which reach the phosphor 7 when the specimen 5 is interposed between the phosphor 7 and the source 2. Accordingly, the concept of the present invention assumes that, when the specimen 5 is interposed in the radiation beam, each radiation striking the phosphor 7 has traversed the specimen 5 without engaging in any of the various nuclear or other interactions in the specimen 5 which are possible. As hereinbefore stated, such as assumption is not strictly correct, since any exposure of the phosphor 7 may permit the receipt of a stray radiation from any origin, and also some radiations which are diverted out of the beam because of engaging in scattering reactions in the specimen 5, may re-enter the beam because of further scattering reactions therein.

It will be apparent, therefore, that the size of the aperture 13 will have a direct relationship to the number of radiations which stray back into the beam and are detected, and also upon the number of detected radiations which were never a part of the beam. On the other hand, it will also be apparent that the size of the aperture 13 is directly related to the statistical accuracy of the measurement to be made, depending upon the size of the specimen 5 and the spacing between the source 2 and the phosphor 7, as will hereinafter be explained.

The pulses generated by the photomultiplier tube 8 are relatively small in amplitude, and thus the signal 9 which is composed of these pulses is preferably applied to an amplifier 10. The output signal 11 from the amplifier 10 is, in turn, preferably routed to a multi-channel pulse height analyzer or other suitable device such as two differential discriminators 14 and 15 having different preselected trigger levels whereby their output signals 16 and 17 correspond to radiations of different preselected energy. Each of these signals 16 and 17 is, in turn, coupled to the input of one of a pair of suitable timer-scalers 18 and 19 having their output signals 21 and 22 connected to a suitable digital computer 20.

Referring again to Equations 1 and 2, it will be apparent that $I_{o,1}$ therein may be derived from the number of pulses in signal 21, wherein the radiation source 2 is composed of iodine-125, and when the specimen 5 is removed from between the source 2 and the phosphor 7. Similarly, $I_{o,2}$ therein is derived from the number of pulses in signal 22 under the same circumstances, except that the radiation source 2 is composed of americium-241. On the other hand, if the specimen 5 is interposed as indicated in FIG. 1, then signal 21 will provide the basis for $I_1$ when the radiation source 2 is composed of iodine-125, and signal 22 will similarly provide the basis for $I_2$ when the radiation source 2 is composed of americium-241.

Inasmuch as radiation sources composed of unstable isotopes have a relatively limited "lifetime", and since precision is of particular importance for the purposes of the present invention, then the values of $I_{o,1}$ and $I_{o,2}$ must be determined each time a measurement for bone mineral content is to be made. On the other hand, it is also undesirable to expose the phosphor 7 directly to the radiation beam for the period of time during which $I_1$ and $I_2$ are derived, inasmuch as the unattenuated intensity of the beam from iodine-125 is about $10^5$ counts per second. Accordingly, "standards" are preferably employed for calibration purposes which are formed of a material to provide a preselected attenuation capability. In particular, a "finger" standard may be a rectangular mass having 0.102 grams/cm$^2$ of copper and 2.4 grams/cm$^2$ of methyl methacrylate, and "wrist" standard having the same transmission characteristics of the distal end of the radius may be formed with 0.102 grams/cm$^2$ of copper and 4.7 grams/cm$^2$ of methyl methacrylate. A standard having only the 2.4 grams/cm$^2$ of methyl methacrylate may also be used, and a "finger" standard may also be composed of 1.5 cm of methyl methacrylate with a 0.5 cm thick section of bovine bone.

As will hereinafter be explained, it is preferable that signals 21 and 22 be derived separately, and thus the radiation source 2 will preferably be either a low energy material or a high energy material depending upon which measurement is to be taken. It is within the scope of the present invention, however, to provide an encapsulated mixture of both americium-241 and iodine-125 as the radiation source 2, or to provide separate but juxtaposed capsules of such isotopes adjacent the aperture 4, whereby the radiation beam will be simultaneously composed of radiations of both high and low energy. Under these circumstances, of course, signals 21 and 22 may be derived and inputted to the computer 20 at the same time.

Referring now to FIG. 2, there may be seen a pictorial illustration of one form of a radiological device 25 which is especially suitable for purposes of the present invention. More particularly, the device 25 may be seen to include a table 26 arranged horizontally on a plurality of legs 27–28, and on the flanges 41–42 of the base arm 30 portion of a support bracket 29, and having an aperture 39 therein as indicated. The support bracket 29 further includes an upper arm 32 portion disposed above the table 26 by an intermediate vertical portion 31, for mounting a detector assembly 33 above the aperture 39 in the table 26.

As indicated in FIG. 2, the detector assembly 33 is composed of a suitable crystal or other type of phosphor 35 disposed within a suitable cannister-type shield 36, and a photomultiplier tube 34 having a pair of conductors 37–38 for providing the signal 9 indicated simplistically in FIG. 1. Provision for adjusting the vertical spacing between the phosphor 35 and the radiation source (not depicted in FIG. 2) below the table 26, is had by disposing the detector assembly 33 slidably in the upper arm 32 of the support bracket 29. Accordingly, a ring clamp 53 or other suitable means is preferably provided for securing the detector assembly 33 to the upper arm 32 to maintain such spacing.

It will be readily apparent that repeatability is a factor insofar as the reliability of any measurement of an unknown parameter is concerned, and that this is especially important in the case of any type of radiological measurement. It also is well known that the geometry of any radiological measurement system is an important factor in the repeatability of such measurements. This is a particular problem with measurments of bone mineral content in a person, since these measurements may be required to be taken at different intervals over an extended period of time.

Referring now to FIG. 5, there may be seen a pictorial representation of a specimen holder 55 which is particularly suitable for making measurements of bone mineral content with the radiological device 25 depicted in FIG. 2. More particularly, the specimen holder 55 may conveniently be a rectangular slab-like plaster casting having a depression or deep imprint 56 formed by the specimen 5 sought to be investigated. As specifically indicated in FIG. 5, the specimen 5 may be the hand of a subject person. Accordingly, if the person inserts his hand into the imprint 56 previously formed on another occasion, the hand or other specimen 5 will be located in the specimen holder 55 exactly as it was on that other occasion.

What is desired, of course, is to interpose only the specimen 5 in the radiation beam, and not the specimen holder 55. Accordingly, the specimen holder 55 is preferably provided with an aperture 58 which is located in the imprint 56 to coincide with the aperture 39 in the table 26, whereby only the subject's hand or other body portion constituting the specimen 5 is actually interposed in the radiation beam.

As hereinbefore stated, it is essential that the specimen 5 be located exactly the same each time a measurement is taken. Accordingly, the specimen holder 55 is also preferably provided with at least two additional hole 59–60, whereby the specimen holder 55 may be relocated on the table 26 with guide pins 61–62 exactly the same each time, and whereby the aperture 58 in the specimen holder 55 is properly aligned with the aperture 39 in the table 26.

Referring now to FIG. 3, there may be seen a pictorial illustration of a source holder assembly 40 which is suitable for properly aligning and supporting a source of radioactivity in the radiological device 25 indicated in FIG. 2. More particularly, the source holder assembly 40 may include an aluminum disc or wheel 43 which is rotatably mounted beneath the table 26, and between the flanges 41–42 of the support bracket 29, by means of a brass pivot pin 46 or the like.

As depicted, the wheel 43 is preferably provided with a plurality of source apertures 44, which are preferably spaced apart about the pivot pin 46 so as to be rotatably brought into alignment with the aperture 39 in the deck 26, and which may be threaded to receive a suitable capsule 45 containing a selected isotope. Thus, the capsule 45 may contain iodine-125 for producing a low energy radiation beam when aligned with the deck aperture 39, and another similar capsule (not depicted in FIG. 3) with americium-241 may be disposed in another source aperture 44, to produce a high energy beam when aligned with the deck aperture 39.

It is desirable that the wheel 43 be fixedly positioned with respect to the deck aperture 39, whenever the subject specimen 5 in the holder 55 is to be irradiated. Accordingly, the rim of the wheel 43 may also be provided with other holes appropriately located to receive a spring-loaded locking pin 48 which is slidably positioned in a pin guide member 49 also mounted on the underside of the deck 26.

The deck 26 is, of course, preferably formed of a material which will assist in shielding the phosphor 35 from radiation from any source other than one aligned with the deck aperture 39. Additional shielding may be desirably provided by a large circular disc 47 of lead and the like, however, which is preferably disposed concentrically between the wheel 43 and the underside of the deck 26. If the disc 47 is fixedly secured to the wheel 43, then the disc 47 will also require an additional plurality of holes corresponding to and aligned with the source holes 44 in the wheels 43. If the disc 47 is fixed to the underside of the deck 26, however, then the disc 47 need have only one hole corresponding to and aligned with the deck aperture 39.

The exact size of the source holes 44 and deck aperture 39 will, of course, depend upon such factors as the size of the radiation source 2, the size of the source capsule 45, the size of the phosphor 35, the spacing between the source capsule 45 and the phosphor 35, and the size of the specimen 5 to be measured. In one useful form of this apparatus, however, a deck aperture 39 was provided having 1.27 cm diameter, with a similar size aperture 58 provided in the plaster specimen holder 55. In this arrangement, a source-detector spacing of 12 cm was provided, the spacing being measured between the lowest end of the detector assembly 33 and the lower surface of the source wheel 43. However, the radiological device 25 illustrated in FIG. 2 will preferably have a provision for varying this spacing with a range of 9 cm to 19 cm as necessary, and depending upon whether the specimen 5 is a finger or a wrist bone or the like.

Referring now to FIG. 4, there may be seen a pictorial illustation, partly in cross section, of the lower portion of the detector assembly 33, and more particularly depicting how the phosphor 35 is partially enclosed within a cannister-type shield 36 having a threaded end aperture 51. Accordingly, this end aperture 51 is preferably provided with an annular insert 50 having a central radiation aperture 52 for admitting the beam of radiations to the phosphor 35.

In one suitable embodiment of this apparatus, a phosphor 35 was provided which was a single sodium iodide crystal, thallium-activated, which was 3 inches thick measured vertically and having a 13 mm diameter. In addition, an 0.025 mm thick layer of aluminum foil 57 may conveniently be disposed for protective purposes between the phosphor 35 and the insert 50. The diameter of the radiation aperture 52 in the insert 50 may, as hereinbefore stated, be a function of the radiation counting rate sought to be attained. Accordingly, inserts having aperture diameters of 1.58 mm – 12.7 mm, and having thicknesses or lengths of 3.5 cm, have been successfully used for the purposes of the present invention. In particular, an insert aperture diameter of 6.4 mm has been found especially useful for measuring bone mineral content in humans. Moreover, in such an arrangement the detector assembly 33 has been found to be more than 99 percent sensitive to 60 kev. radiation beam produced with a source composed of americium-241, and similarly sensitive to a 28 kev. radiation beam produced with a source composed of iodine-125.

Referring again to FIG. 1, it will be noted that the trigger levels and the widths of the "windows" in the two discriminators 14–15 are an important factor in the proper use of the present invention. Although the precise optimum values for these parameters will depend upon the other parameters in the system, in an ideal embodiment of the invention the first discriminator 14 was provided with a lower trigger level setting at kev., and a "window" of 14 kev. The lower trigger level of the second discriminator 15 was also set at 21 kev., but no upper energy discriminator was provided.

The reason a 14 kev. "window" was provided for the first discriminator 14 was because an iodine-125 radiation source is often contaminated with iodine-126, and this creates an undesirable amount of background pulses in the signal 16. The reason a "window" can sometimes be conveniently omitted with respect to the second discriminator 15, is that errors may arise when spectrometer settings are changed during measurements.

As hereinbefore indicated, it is not enough to derive $I_1$ and $I_2$ on the basis of merely a determination of counting rate for the attenuated and non-attenuated radiation beam. Rather, it is preferred to determine these values on the basis of number of counts obtained during a preselected time interval, since this provides these values in a digital form suitable for the purposes of a conventional digital computer 20. Timing may be achieved by interruption of the radiation beam with a mechanical shutter and the like. However, the timer-scalers 18–19 are more suitable for these purposes, since they provide for segregating or selecting those pulses which occur in signals 16–17 during a precisely defined time interval, and this enhances the accuracy of the measurements sought to be taken.

While particular embodiments of the present invention have been shown and described, it is apparent that changes and modifications may be made without departing from this invention in its broader aspects; and, therefore, the aim in the appended claims is to cover all such changes and modifications as fall within the true spirit and scope of this invention.

What is claimed is:

1. Apparatus for deriving a functional indication of the bone mineral content of a selected portion of a human body and the like containing both bone and soft tissue, comprising
    a source of radiations of first and second different preselected energies,
    a detector spaced from said source for registering radiations therefrom,
    a first collimation means interposed about said source for forming a beam of said radiations directed toward said detector,
    support means for locating said selected body portion between said source and detector and in said beam,
    signaling means for deriving a first electrical signal corresponding to the intensity of the non-attenuated ones of said radiations of said first energy registered by said detector and a second electrical signal corresponding to the intensity of the non-attenuated ones of said radiations of said second energy registered by said detector, and
    means for deriving from said first and second electrical signals the bone mineral content of said selected body portion as a function of the soft tissues also present therein.

2. The apparatus described in claim 1, wherein said first electrical signal is composed of pulses corresponding in number to the value:

$$(I_{o,1}) \exp [(-\mu_{BM,1} M_{BM}) - (\mu_{St,1} M_{St})]$$

wherein $I_{o,1}$ equals the non-attenuated intensity of the radiations of said first energy, $\mu_{BM,1}$ is the mass attenuation coefficient of the bone tissue with respect to said first energy $M_{BM}$ is the mass in grams/cm$^2$ of said bone mineral sought to be determined, $\mu_{ST,1}$ is the mass attenuation coefficient of the soft tissue with respect to said first energy, and $M_{ST}$ is the mass in grams/cm$^2$ of the soft tissue also present in said irradiated body portion.

3. The apparatus described in claim 2, wherein said second electrical signal is composed of pulses corresponding in number to the value:

$$(I_{o,2}) \exp [(-\mu_{BM,2} M_{BM}) - (\mu_{St,2} M_{ST})]$$

wherein $I_{o,2}$ equals the non-attenuated intensity of the radiations of said second energy, $\mu_{BM,2}$ is the mass attenuation coefficient of the bone tissue with respect to said second energy, and $\mu_{ST,2}$ is the mass attenuation coefficient of the soft tissue with respect to said second energy.

4. The apparatus described in claim 3, wherein said source of radiations includes an encapsulated quantity of gadolinium-153.

5. The apparatus described in claim 3, wherein said source of radiations includes an encapsulated quantity of americium-241.

6. The apparatus described in claim 5, wherein said source of radiations further includes an encapsulated quantity of iodine-125.

7. The apparatus described in claim 6, wherein said source of radiations includes an encapsulated mixture of americium-241 and iodine-125.

8. The apparatus described in claim 6, wherein said source of radiations includes
    a first encapsulated mixture of iodine-125,
    a second separate encapsulated mixture of americium-241, and
    holder means for supporting said first and second encapsulated mixtures in spaced-apart relationship and movable to selectively position one of said mixtures in cooperation with said first collimation means to form said beam of radiations of only the preselected energy relating to said selected mixture.

9. Apparatus for determining the bone mineral content of a living specimen portion of a human, comprising
    frame means having spaced apart upper and lower arm portions,
    table means interconnected with and horizontally supported by said lower arm portion of said bracket means and further having a collimating aperture,
    a polyenergetic radiation source disposed below said table means and adjacent said collimating aperture therein for producing a beam of radiations of predetermined energies and intensities projecting upward from said collimating aperture,
    a radiation detector adjustably interconnected with and vertically supported by said upper arm portion of said bracket means for receiving said beam of radiations,
    holder means fixedly interconnectable with said table means for establishing said specimen in said radiation beam according to a preselected geometry, and shielding means interposed about and having an aperture of a preselected size for exposing said detector means to substantially only non-attenuated radiations in said beam.

10. The apparatus described in claim 9, wherein said radiation source includes a source holder disposed below said table means, and encapsulated quantities of two different preselected unstable isotopes mounted in said source holder for location adjacent said collimation aperture in said table means.

11. The apparatus described in claim 10, wherein said source holder is a circular body member rotatably interconnected under said table means and having said encapsulated quantities of said isotopes fixed at different spaced apart locations therein, whereby rotation of said source holder selectively positions one isotope at said collimation aperture and the other isotope away from said collimation aperture.

12. Apparatus for deriving a functional indication of the bone mineral content of a specimen portion of a living human body containing both bone tissues and soft tissues, comprising
support means for holding said specimen in a substantially fixed position,
radiation source means fixedly spaced from and interconnected with said support means for bombarding said specimen with radiations of first and second predetermined energies and intensities,
sensor means for registering radiations emanating from said source means and penetrating and traversing said specimen without engaging in interactions with said bone tissues and soft tissues therein,
detector means responsive to said sensor means for generating a signal functionally related to the intensity of said registered radiations, and
indicating means for deriving from said signal a functional indication of the bone mineral content of said specimen.

13. The apparatus described in claim 12, wherein said support means is provided with an indentation having a configuration matching and corresponding to the configuration of said specimen portion.

14. The apparatus described in claim 13, wherein said support means is fixedly secured between said source means and said sensor means.

15. The apparatus described in claim 14, wherein said sensor means comprises
a phosphorescent inorganic crystal for producing scintillations in response to and of an intensity functionally related to the terminal energies of incident radiations, and
a shield means enclosing and protecting said crystal against incident radiations and having an aperture confronting said radiation source means.

16. The apparatus described in claim 15, wherein said detector means comprises
a photomultiplier tube optically coupled to said crystal for generating electrical pulses corresponding in occurrence and amplitude to incident radiations and their energies,
bracket means for supporting said tube and crystal at a fixed preselected spacing from said radiation source means, and
pulse analysis means for deriving from said electrical pulses a signal functionally related to the attenuation of said radiations by said specimen in said holder means.

17. The apparatus described in claim 16, wherein said shield means enclosing said crystal further includes an annular insert threadably disposed in said aperture in said shield means for establishing a window to said crystal functionally related in size to the attenuation characteristics of said specimen.

18. A method of determining the amount of bone mineral content in a specimen portion of a living human body containing both bone and soft tissues, comprising
bombarding said specimen portion with radiations of a first preselected energy,
bombarding said specimen portion with radiations of a second different preselected energy,
detecting and counting radiations of said first energy which penetrate and traverse said specimen portion without engaging in interactions with said bone and soft tissues therein,
detecting and counting radiations of said second energy which penetrate and traverse said specimen portion without engaging in interactions with said bone and soft tissues therein, and
deriving from the number of said counted radiations the bone mineral content of said specimen portion as a function of the value of:

$$(I_{o,1}) \; exp \; [(-\mu_{BM,1} M_{BM}) - (\mu_{ST,1} M_{ST})]$$

wherein $I_{o,1}$ equals the intensity of said radiations of said first radiation bombarding said specimen portion, $\mu BM,1$ is the mass attenuation coefficient of said bone tissue with respect to said first energy, $M_{BM}$ is the mass in grams/cm$^2$ of the bone mineral sought to be determined, $\mu ST,1$ is the mass attenuation coefficient of said soft tissues with respect to said first energy, and $M_{ST}$ is the mass in grams/cm$^2$ of th soft tissues in said specimen portion.

19. A method of determining the bone mineral content of a specimen portion of a living human body containing both bone and soft tissues, comprising
bombarding said specimen portion with radiations of first and second different preselected energies,
determining the attenuated intensity of said radiations of said first energy,
determining the attenuated intensity of said radiations of said second energy,
determining the attenuation coefficients of said bone mineral as a function of both said first and second energies, and
deriving from said attenuated intensities the bone mineral content of said bombarded specimen portion as a function of the values $$(I_{o,1}) \; exp \; [(-\mu_{BM,1} M_{BM}) - (\mu_{ST,1} M_{ST})]$$
and
$$(I_{o,2}) \; exp \; [(-\mu_{BM,2} M_{BM}) - (\mu_{ST,2} M_{ST})]$$

wherein $I_{o,1}$ and $I_{o,2}$ equal the intensities of said radiation of said first and second energies bombarding said specimen portion, $\mu BM,1$ and $\mu BM,2$ are the redrived attenuation coefficients of said bone mineral as a function of both said energies, $\mu ST,1$ and $\mu ST,2$ are the attenuation coefficients of said soft tissues as a function of both said energies, and $M_{BM}$ and $M_{ST}$ are the mass in grams/cm$^2$ of the bone mineral and soft tissues in said specimen portion.

* * * * *

Disclaimer 3,996,471.—*James C. Fletcher*, Administrator of the National Aeronautics and Space Administration, with respect to an invention of *John R. Cameron*, Madison, Wis. and *Philip F. Judy*, Boston, Mass. METHOD AND SYSTEM FOR IN VIVO MEASUREMENT OF BONE TISSUE USING A TWO LEVEL ENERGY SOURCE. Patent dated Dec. 7, 1976. Disclaimer filed Oct. 29, 1986, by the *Administrator*.

Hereby enters this disclaimer to the remaining term of said patent.
[*Official Gazette February 17, 1987.*]